US012420417B2

United States Patent
Jin (10) Patent No.: US 12,420,417 B2
(45) Date of Patent: Sep. 23, 2025

(54) ROBOTIC ARM CONTROL METHOD AND APPARATUS, AND ROBOTIC ARM

(71) Applicant: Ronovo (Shanghai) Medical Science and Technology Ltd., Shanghai (CN)

(72) Inventor: Xin Jin, Shanghai (CN)

(73) Assignee: Ronovo (Shanghai) Medical Science and Technology Ltd., Shanghai (CN)

( * ) Notice: Subject to any disclaimer, the term of this patent is extended or adjusted under 35 U.S.C. 154(b) by 62 days.

(21) Appl. No.: 18/640,993

(22) Filed: Apr. 19, 2024

(65) Prior Publication Data
US 2024/0300107 A1   Sep. 12, 2024

Related U.S. Application Data

(63) Continuation of application No. PCT/CN2022/125941, filed on Oct. 18, 2022.

(30) Foreign Application Priority Data

Oct. 22, 2021   (CN) .......................... 202111231646.7

(51) Int. Cl.
    B25J 9/16       (2006.01)
    B25J 9/06       (2006.01)
    (Continued)

(52) U.S. Cl.
    CPC .............. *B25J 9/1664* (2013.01); *B25J 9/06* (2013.01); *B25J 13/06* (2013.01)

(58) Field of Classification Search
    CPC ..... B25J 9/1664; B25J 9/16; B25J 9/06; B25J 13/06; A61B 34/30; A61B 90/00; A61B 34/37; G05B 19/408
    USPC ........................................................ 700/245
    See application file for complete search history.

(56) References Cited

U.S. PATENT DOCUMENTS 9,579,788 B2 *   2/2017   Rosenberg ................. B25J 9/16
10,807,242 B2 *  10/2020  Zhou ....................... A61B 90/03
(Continued)

FOREIGN PATENT DOCUMENTS

CN   106625666 A   5/2017
CN   106945036 A   7/2017
(Continued)

OTHER PUBLICATIONS

China National Intellectual Property Administration, Office Action / Notice of First Review Opinion in corresponding Chinese Patent Application No. 202111231646.7 dated Jun. 29, 2024.
(Continued)

*Primary Examiner* — Kira Nguyen
(74) *Attorney, Agent, or Firm* — Leydig, Voit & Mayer, Ltd.

(57) ABSTRACT

Provided are a robotic arm control method and apparatus, and a robotic arm. The control method includes a dragging preparation phase and a dragging phase. The dragging preparation phase includes determining a target arm body and a position characteristic value of the target arm body, determining a relationship expression between the position characteristic value and the positions of multiple joints, and determining a target joint as the control object in the dragging phase. The dragging phase includes determining the target value of the position characteristic value and the positions of multiple joints except the target joint at the current moment; substituting the obtained parameters into a first calculation expression to solve for the next position of the target joint when a robotic arm is dragged from a current position.

20 Claims, 8 Drawing Sheets

(51) Int. Cl.
*B25J 13/06* (2006.01)
*A61B 34/30* (2016.01)

(56) References Cited

U.S. PATENT DOCUMENTS

2020/0367978 A1* 11/2020 Gonenc ................ G06F 3/0444
2021/0187731 A1* 6/2021 Lin ....................... B25J 9/1643

FOREIGN PATENT DOCUMENTS

| | | |
|---|---|---|
| CN | 109549706 A | 4/2019 |
| CN | 110524544 A | 12/2019 |
| CN | 111887906 A | 11/2020 |
| CN | 111991086 A | 11/2020 |
| CN | 112057170 A | 12/2020 |
| CN | 112847345 A | 5/2021 |
| CN | 113384347 A | 9/2021 |
| DE | 102013100605 A1 | 7/2014 |
| WO | 2018176854 A1 | 10/2018 |
| WO | 2019213432 A1 | 11/2019 |

OTHER PUBLICATIONS

China National Intellectual Property Administration, Notice to Grant / Notice of Registration Procedure in corresponding Chinese Patent Application No. 202111231646.7 dated Aug. 37, 2024.
China National Intellectual Property Administration, International Search Report in corresponding International Application No. PCT/CN2022/125941 dated Dec. 22, 2022, mailed on Jan. 16, 2023.

* cited by examiner

ROBOTIC ARM CONTROL METHOD AND APPARATUS, AND ROBOTIC ARM

CROSS-REFERENCE TO RELATED APPLICATIONS

This application n of International Application No. PCT/CN2022/125941, filed Oct. 18, 2022, which claims priority to Chinese Patent Application No. 202111231646.7, filed Oct. 22, 2021, which are both expressly incorporated by reference in their entirety, including any references contained therein.

TECHNICAL FIELD

Embodiments of the present disclosure relate to the technical field of robotic arm control, for example, a robotic arm control method and apparatus, and a robotic arm.

BACKGROUND

With the advancement of science and technology, the technology of minimally invasive surgical robots has gradually matured and been widely used. A doctor sends a control command to a robotic arm through an operating console. Medical instruments are installed at the end of the robotic arm. Before performing a surgical operation on a patient, the doctor needs to drag the robotic arm so that its end can move to the patient's surgical entrance planned by the doctor and reach a desired posture. Compared with other methods, such as the joystick control of a teach pendant, the manual dragging mode of the robotic arm is fast and intuitive. Manual dragging is usually used to enable a robot to quickly reach a specific posture, such as installing a sterile sleeve or cannula. The dragging manner is not limited to the medical field; other industrial robots also need this function. In addition, for the robotic arm, when the robotic arm has a redundant degree of freedom, collision can be better avoided, and working space can be added.

However, when a robotic arm with a redundant degree of freedom is manually dragged, movements of multiple joints of the robotic arm are uncertain and difficult to predict, making the operation of the robot more difficult.

SUMMARY

Embodiments of the present disclosure provide a robotic arm control method and apparatus, and a robotic arm, which avoid the situation where multiple joints of the robotic arm have movement uncertainty when the robotic arm with a redundant degree of freedom is manually dragged.

In a first aspect, embodiments of the present disclosure provide a robotic arm control method applied to a manual dragging control system of a robotic arm. The robotic arm control method includes a dragging preparation phase and a dragging phase. In the method, the number of joints of the robotic arm is greater than or equal to 4 when the robotic arm moves in a three-dimensional space; the number of joints of the robotic arm is greater than or equal to 3 when the robotic arm moves in a plane.

The dragging preparation phase includes the steps below.

One arm body of the robotic arm is selected as a target arm body, and the position of the target arm body is determined as a position characteristic value.

Based on the forward kinematics of the robotic arm, the relationship between the position characteristic value and positions of multiple joints of the robotic arm is determined to obtain a first calculation expression of the position characteristic value.

One of the multiple joints of the robotic arm is selected as a target joint, and the target joint is a control object in the dragging phase.

After the dragging preparation phase is completed, the dragging phase is entered, and the dragging phase includes the steps below.

A target value of the position characteristic value is determined.

Positions of the multiple joints except the target joint are acquired at the current moment.

The target value of the position characteristic value and the positions of the multiple joints except the target joint are substituted into the first calculation expression to solve for the next position of the target joint when the robotic arm is dragged from a current position.

In a second aspect, embodiments of the present disclosure also provide a robotic arm control apparatus applied to a manual dragging control system of a robotic arm. In the apparatus, the number of joints of the robotic arm is greater than or equal to 4 when the robotic arm moves in a three-dimensional space; the number of joints of the robotic arm is greater than or equal to 3 when the robotic arm moves in a plane; and the robotic arm control apparatus includes a characteristic value determination unit, an expression establishment unit, a target joint determination unit, a target value determination unit, a position acquisition unit, and a position calculation unit.

The characteristic value determination unit is configured to select one arm body of the robotic arm as a target arm body and determine the position of the target arm body as a position characteristic value.

The expression establishment unit is configured to determine, based on the forward kinematics of the robotic arm, the relationship between the position characteristic value and positions of multiple joints of the robotic arm to obtain a first calculation expression of the position characteristic value.

The target joint determination unit is configured to select one of the multiple joints of the robotic arm as a target joint, and the target joint is a control object in a dragging phase.

The target value determination unit is configured to determine a target value of the position characteristic value.

The position acquisition unit is configured to acquire positions of the multiple joints except the target joint at the current moment.

The position calculation unit is configured to substitute the target value of the position characteristic value and the positions of the multiple joints except the target joint into the first calculation expression to solve for the next position of the target joint when the robotic arm is dragged from a current position.

In a third aspect, embodiments of the present disclosure also provide a manual dragging control system including the robotic arm control apparatus described in any of the preceding embodiments.

In a fourth aspect, embodiments of the present disclosure also provide a robotic arm.

The robotic arm includes one or more processors and a memory.

The memory is configured to store one or more programs.

When executed by the one or more processors, the one or more programs cause the one or more processors to implement the robotic arm control method as described in any of the preceding embodiments.

In a fifth aspect, embodiments of the present disclosure also provide a computer-readable storage medium storing a computer program that, when executed by a processor, implements the robotic arm control method as described in any of the preceding embodiments.

DETAILED DESCRIPTION

It should be noted that terms such as "first" and "second" in the description, claims, and drawings of the present disclosure are used for distinguishing between different objects and not necessarily for describing a particular order. Multiple embodiments of the present disclosure described below may be implemented on its own or implemented in combination with each other, which is not specifically limited in the embodiments of the present disclosure.

For a robotic arm with M degrees of freedom at its end, if the robotic arm moves in a plane, the end of the robotic arm may have two or three degrees of freedom. If the robotic arm moves in a three-dimensional space, the end of the robotic arm may have 3 to 6 degrees of freedom. If the number of joints of a robotic arm is greater than the number of degrees of freedom at the end, it is considered that the robotic arm has a redundant degree of freedom. With the redundant degree of freedom, working space of the robotic arm is increased; moreover, when a determined end position of the robotic arm is given, positions that can be reached by multiple joints of the robotic arm are not fixed, and multiple possibilities exist.

Figure 1:
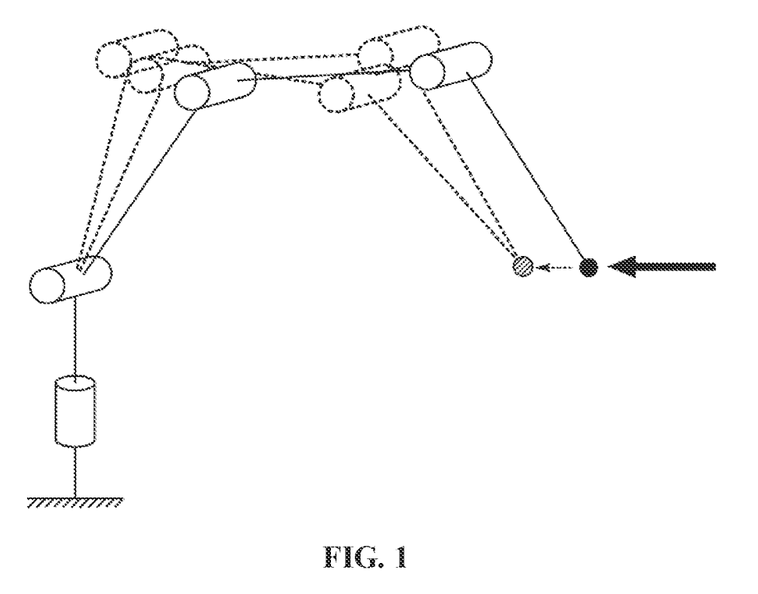
FIG. 1 is a diagram illustrating movement uncertainty when a robotic arm is manually dragged according to an embodiment of the present disclosure.

Therefore, for a robotic arm with a redundant degree of freedom, when the end of the robotic arm with a redundant degree of freedom is manually dragged, the movement of multiple joints of the robotic arm is uncertain to an operator. FIG. 1 is a diagram illustrating movement uncertainty when a robotic arm is manually dragged according to an embodiment of the present disclosure. With reference to FIG. 1, after the end of the robotic arm is manually dragged to a new position, multiple possibilities exist for the positions of the joints of the robotic arm. As shown in the dashed lines in FIG. 1, the operator cannot predict the movement corresponding to multiple joints when manually dragging the end of the robotic arm, which increases the difficulty of the operation of the robotic arm and increases the risk of collision when dragging is manually performed.

Figure 2:
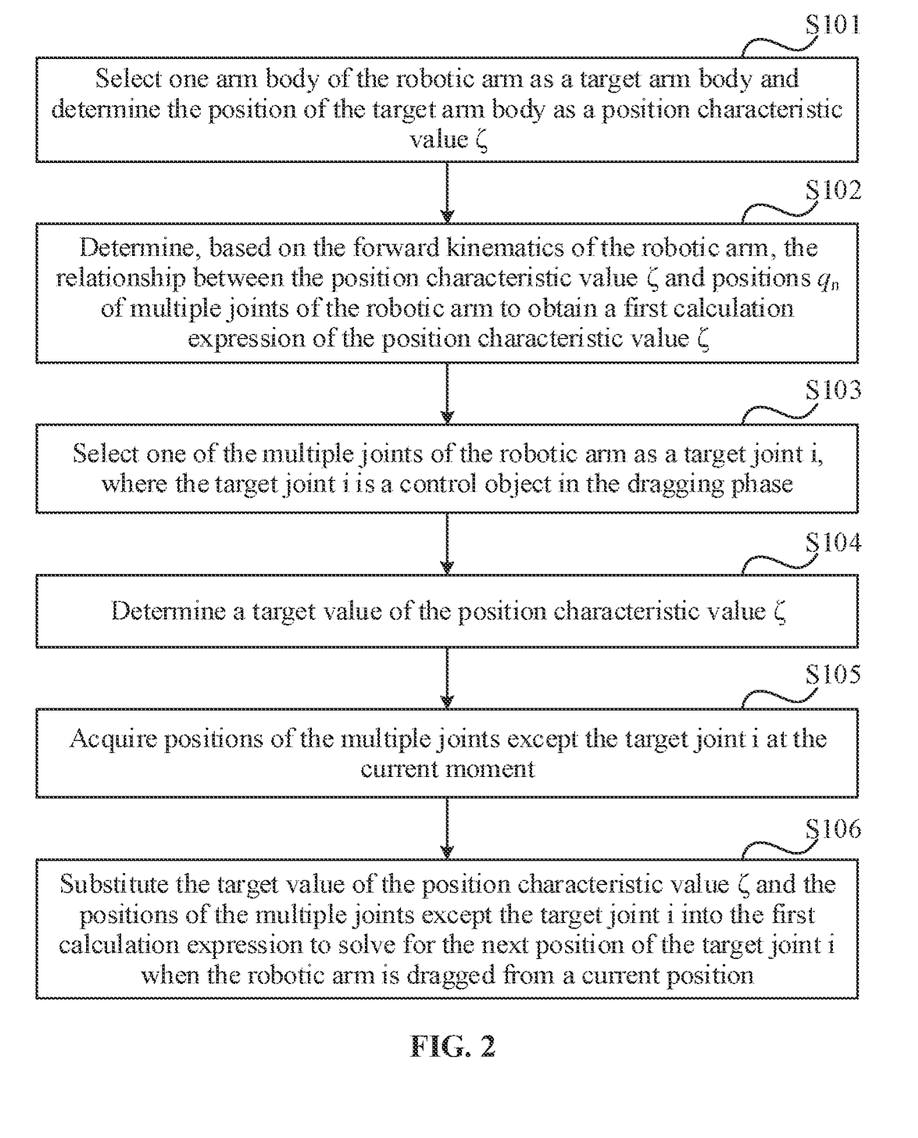
FIG. 2 is a flowchart of a robotic arm control method according to an embodiment of the present disclosure.

An embodiment of the present disclosure provides a robotic arm control method. FIG. 2 is a flowchart of a robotic arm control method according to an embodiment of the present disclosure. The robotic arm control method is applied to a manual dragging control system of a robotic arm. In the method, the number of joints of the robotic arm is greater than or equal to 4 when the robotic arm moves in a three-dimensional space; the number of joints of the robotic arm is greater than or equal to 3 when the robotic arm moves in a plane; and the robotic arm control method includes a dragging preparation phase and a dragging phase. As shown in FIG. 2, the robotic arm control method includes the following steps:

The dragging preparation phase includes the steps below.

In S101, one arm body of the robotic arm is selected as a target arm body, and the position of the target arm body is determined as a position characteristic value $\zeta$.

For example, one arm body of the robotic arm is selected as a target arm body, and the position of the selected target arm body is determined as a position characteristic value $\zeta$. The position of the target arm body may be a position coordinate in a preset (x, y, z) coordinate system or may be an angle value relative to a preset reference object, that is, one piece of the position information of the target arm body is selected as the position characteristic value $\zeta$.

Figure 3:
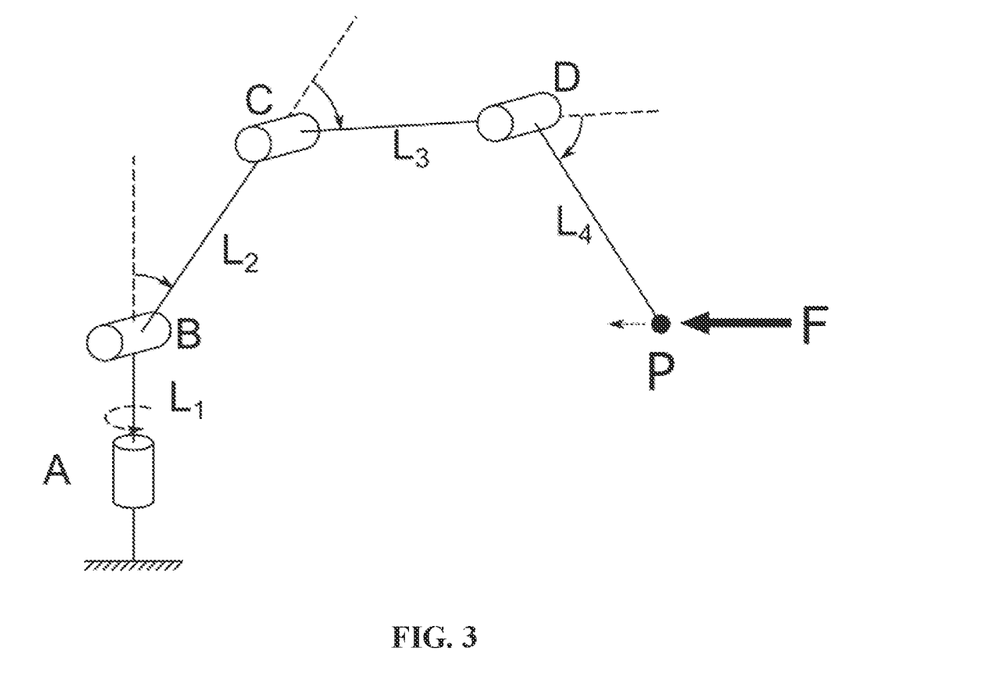
FIG. 3 is a diagram illustrating the structure of a robotic arm according to an embodiment of the present disclosure.

FIG. 3 is a diagram illustrating the structure of a robotic arm according to an embodiment of the present disclosure. With reference to FIG. 3, the robotic arm in FIG. 3 includes four joints A, B, C, and D, where positions of the four joints A, B, C, and D are $q_1$, $q_2$, $q_3$, and $q_4$, respectively; the A joint of the robotic arm is fixed to the ground; the robotic arm includes four arm bodies, that is, L1, L2, L3, and L4; the end P of the robotic arm is a dragging point of a user. When a dragging force F is applied to the end P, the movement of the robotic arm can be controlled. The robotic arm shown in FIG. 3 is a robotic arm in a three-dimensional space, and the number of joints is 4. Apparently, the robotic arm shown in FIG. 3 is a robotic arm with a redundant degree of freedom. For example, in this embodiment of the present disclosure, the arm body L3 may be used as the target arm body, and the included angle between the target arm L3 and the horizontal plane is selected as the position characteristic value $\zeta$.

In S102, based on the forward kinematics of the robotic arm, the relationship between the position characteristic value $\zeta$ and positions $q_n$ of multiple joints of the robotic arm is determined to obtain a first calculation expression of the position characteristic value $\zeta$.

For example, the forward kinematics of the robotic arm is a calculation method that calculates the spatial position of any point on the robotic arm through the joint angles of the robotic arm.

For example, the step in which the relationship between the position characteristic value $\zeta$ and the positions $q_n$ of the multiple joints of the robotic arm is determined based on the forward kinematics of the robotic arm to obtain the first calculation expression of the position characteristic value includes the step below.

Based on the forward kinematics of the robotic arm, the first calculation expression of the position characteristic value is determined as follows: $\zeta = \zeta(q_1, q_2, \ldots q_n)$. $\zeta$ denotes the position characteristic value; q denotes the position of a joint of the robotic arm; $q_n$ denotes the position of an n-th joint of the robotic arm, $n \in [1, N]$, and N denotes the number of joints of the robotic arm.

In S103, one of the multiple joints of the robotic arm is selected as a target joint i, and the target joint i is a control object in the dragging phase.

For example, after the first calculation expression that $\zeta = \zeta(q_1, q_2, \ldots q_n)$ of the position characteristic value $\zeta$ is obtained, one joint i of the robotic arm is selected as the target joint. $i \le n$, and the joint position of the target joint i is $q_i$; the determined target joint i is used as a control object in the dragging phase. At this point, the dragging preparation phase is completed.

It should be noted that the preceding working process of the dragging preparation phase may be pre-set as needed before the robotic arm leaves the factory. Alternatively, the user may save the working process of the dragging preparation phase after setting it once as needed in the using process. In this manner, it is in no need to perform the dragging preparation phase before each dragging in subsequent use. Alternatively, the dragging preparation phase may be set up as needed before each dragging phase starts, which is not repeated herein.

After the dragging preparation phase is completed, the dragging phase is entered, and the dragging phase includes the steps below.

In S104, a target value of the position characteristic value $\zeta$ is determined.

For example, in the process of dragging the end of the robotic arm, a target value needs to be selected for the position characteristic value $\zeta$ of the target arm body, that is, the position that the target arm body should keep is determined when the end of the robotic arm is dragged. For example, if the initial value $\zeta_0$ of the target arm body is selected as the target value of the position characteristic value $\zeta$, it indicates that the position of the target arm body remains unchanged at the initial position when the end of the robotic arm is dragged.

In S105, positions of the multiple joints except the target joint i are acquired at the current moment.

Illustratively, with reference to FIG. 3, an example is used where the joint C is selected as a target joint. Since the joint C is a third joint of the robotic arm, that is, n=3, the joint position of the joint C is $q_3$; in the dragging process, joint positions $q_1$, $q_2$, $q_4$ of joints A, B, and D are acquired. It should be noted that the joint positions herein may be spatial coordinate positions or angles. Due to the structural limitations of the robotic arm shown in FIG. 3, the joint positions referred to in the present disclosure are all angles.

In S106, the target value of the position characteristic value $\zeta$ and the positions of the multiple joints except the target joint i are substituted into the first calculation expression to solve for the next position of the target joint i when the robotic arm is dragged from a current position.

Figure 4:
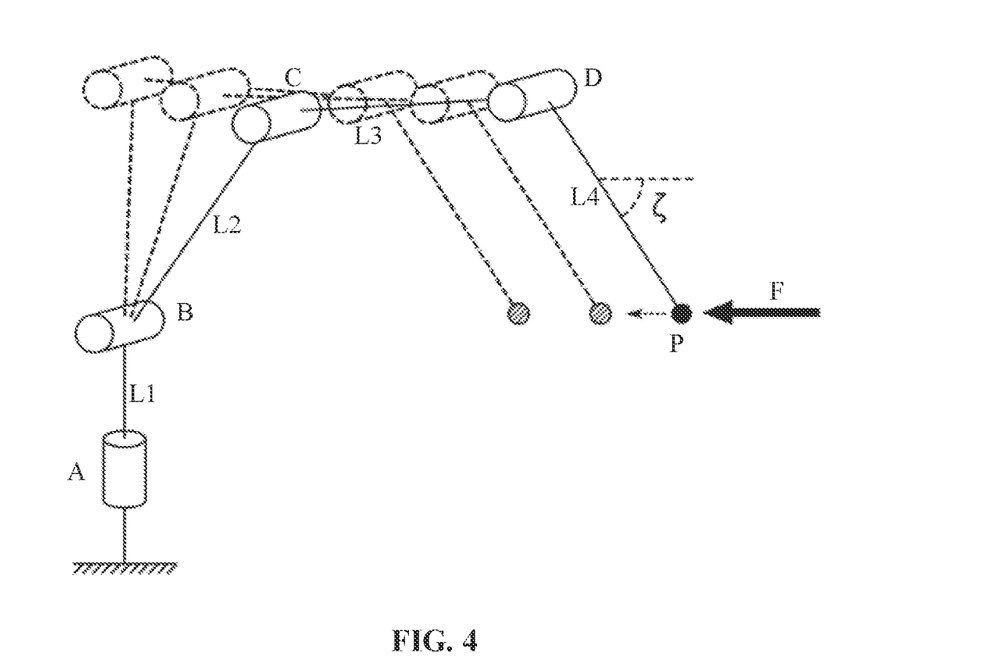
FIG. 4 is a diagram illustrating the dragging of a robotic arm using a robotic arm control method according to an embodiment of the present disclosure.

For example, after the target value of the position characteristic value $\zeta$ is determined, the target value of the position characteristic value $\zeta$ and the positions of the multiple joints except the target joint i are substituted into the first calculation expression that $\zeta = \zeta(q_1, q_2, \ldots q_n)$. At this time, for the first calculation expression, the unknown amount is only the position $q_i$ of the target joint i. Therefore, only the first calculation expression needs to be solved to obtain the next position of the target joint i. Thereafter, at each moment in the dragging phase of the robotic arm, the next position $q_i$ of the target joint i can be calculated by using the preceding method, and then the movement of the target joint i is controlled based on the calculation result. FIG. 4 is a diagram illustrating the dragging of a robotic arm using a robotic arm control method according to an embodiment of the present disclosure. It can be learned from the comparison between FIG. 4 and FIG. 1 that when the robotic arm is dragged by using the robotic arm control method provided by the embodiments of the present disclosure, the movement uncertainty of the robotic arm can be eliminated so that multiple joints of the robotic arm can be moved within a controlled range.

The embodiments of the present disclosure avoid the movement uncertainty of multiple joints of a robotic arm with a redundant degree of freedom when manual dragging is performed. Moreover, when manual dragging is performed, the multiple joints of the robotic arm with a redundant degree of freedom can move within an expected movement range, thereby reducing the operation difficulty of the robotic arm and reducing the risk of collision when manual dragging is performed.

Figure 5:
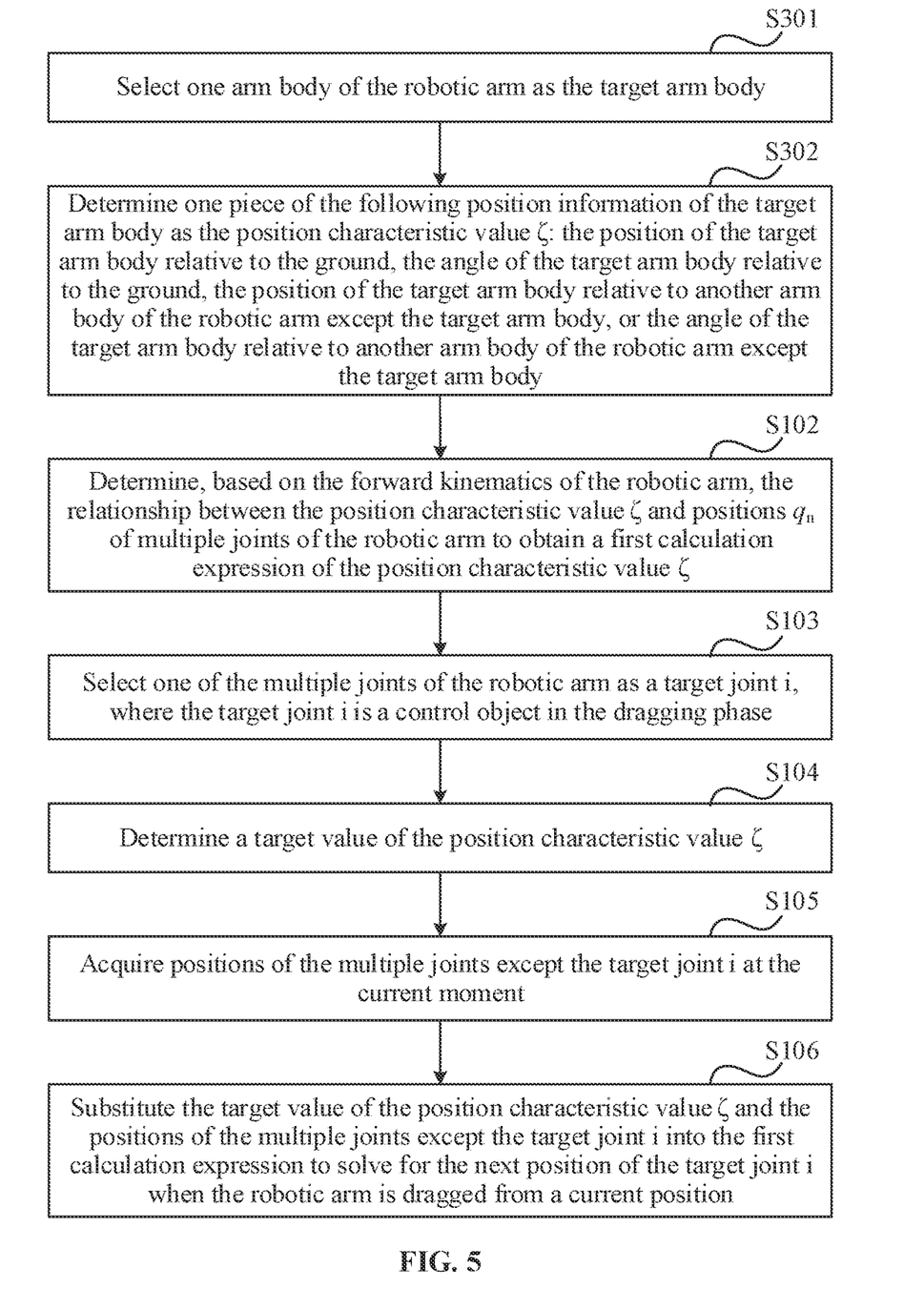
FIG. 5 is a flowchart of another robotic arm control method according to an embodiment of the present disclosure.

Based on the preceding multiple technical solutions, FIG. 5 is a flowchart of another robotic arm control method according to an embodiment of the present disclosure. As shown in FIG. 5, the preceding S101 includes the following steps.

In S301, one arm body of the robotic arm is selected as the target arm body.

For example, with reference to FIG. 3, the target arm body of the robotic arm may be any one of the arm bodies L1, L2, L3, or L4. However, since one end of the joint A is fixed to the ground, the degree of freedom of the arm body L1 is less than the degrees of freedom of the other three arm bodies. For more accurate control of the movement of the robotic arm, the other three arm bodies except the arm body L1 may be selected as the target arm body. In this embodiment of the present disclosure, the arm body L4 may be used as the target arm body.

In S302, one piece of the following position information of the target arm body is determined as the position characteristic value $\zeta$: the position of the target arm body relative to the ground, the angle of the target arm body relative to the ground, the position of the target arm body relative to another arm body of the robotic arm except the target arm body, or the angle of the target arm body relative to another arm body of the robotic arm except the target arm body.

For example, with reference to FIG. 3, the position characteristic value $\zeta$ of the target arm body L4 may have the following four options: the position relative to the ground, the angle relative to the ground, the position relative to another arm body of the robotic arm except the target arm body, or the angle relative to another arm body of the robotic arm except the target arm body. For example, a (x, y, z) coordinate system is established in advance, as shown in FIG. 4, and the angle of the target arm body L4 relative to the ground may be selected as the position characteristic value $\zeta$ of the target arm body L4 based on the preset coordinate system.

Figure 6:
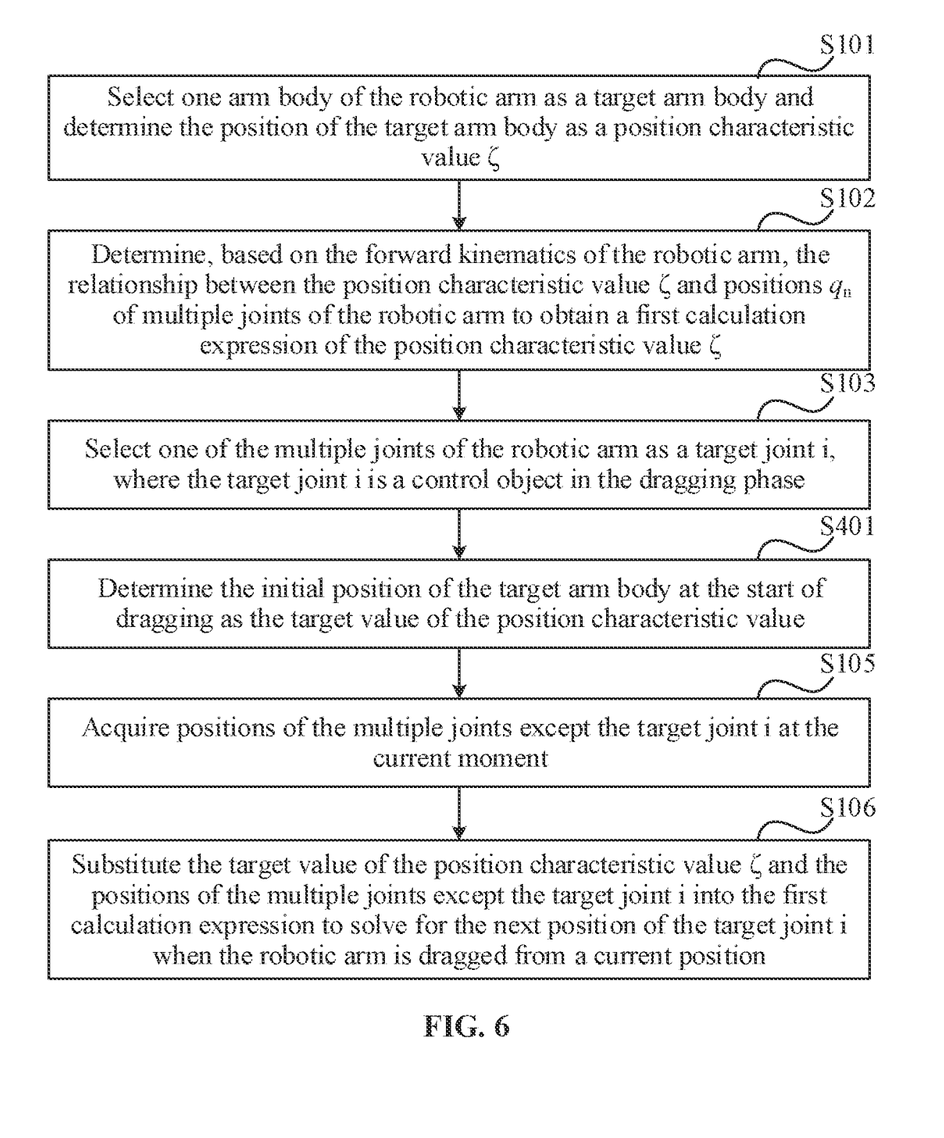
FIG. 6 is a flowchart of yet another robotic arm control method according to an embodiment of the present disclosure.

On the basis of the preceding multiple technical solutions, FIG. 6 is a flowchart of another robotic arm control method according to an embodiment of the present disclosure. As shown in FIG. 6, the preceding S104 of determining the target value of the position characteristic value $\zeta$ includes the following steps.

In S401, the initial position of the target arm body at the start of dragging is determined as the target value of the position characteristic value.

For example, if the initial value $\zeta_0$ of the target arm body at the start of dragging is selected as the target value of the position characteristic value ζ, it indicates that the target arm body remains stationary at the initial position when the end of the robotic arm is dragged. The initial value of the target arm body may be calculated based on the forward kinematics of the robotic arm and initial position values of multiple joints.

Figure 7:
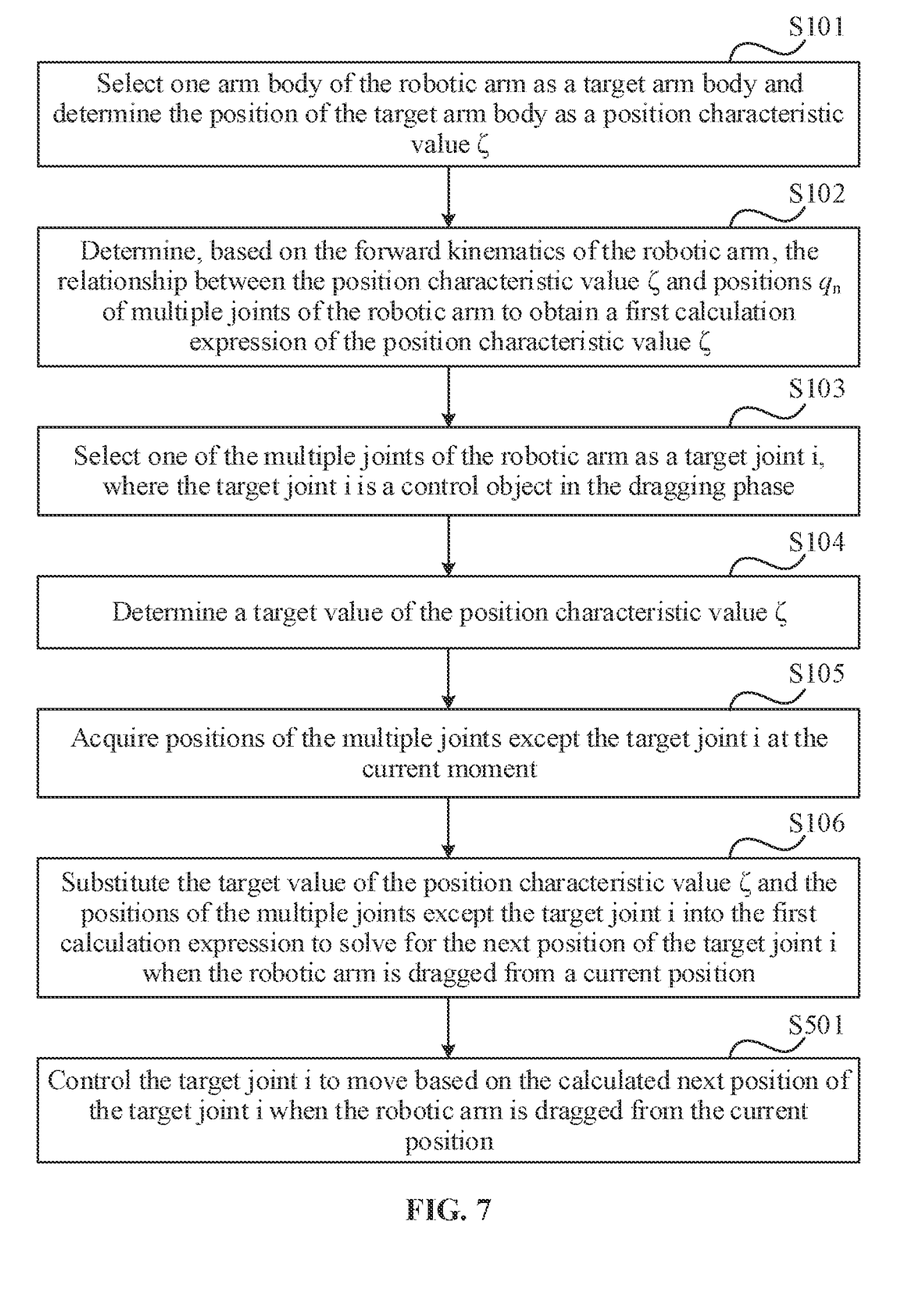
FIG. 7 is a flowchart of yet another robotic arm control method according to an embodiment of the present disclosure.

On the basis of the preceding multiple technical solutions, FIG. 7 is a flowchart of yet another robotic arm control method according to an embodiment of the present disclosure. As shown in FIG. 7, after obtaining the next position of the target joint when the target joint is dragged from the current position in S106, the robotic arm control method also includes the steps below.

In S501, the target joint i is controlled to move based on the calculated next position of the target joint i when the robotic arm is dragged from the current position.

For example, if the target joint i is a joint of linear motion, the first calculation expression is a first-order linear equation, the next position of the target joint i when the robotic arm is dragged from the current position may be directly obtained by solution, and the target joint i may be controlled to move based on the next position of the target joint i obtained by calculation.

It should be noted that when the target joint i is controlled to move based on the next position of the target joint i, it is also necessary to control the actions of multiple other joints except the target joint i. At this time, it is necessary to calculate the gravity moment, friction moment, and damping moment of multiple other joints based on the current position and rotation speed of the robotic arm. After the corresponding moments of the multiple joints are calculated, a joint controller controls the actions of multiple joints based on the calculated corresponding moments. The friction moment and damping moment may be calculated simultaneously as the control basis for joint movement, or only one of the friction moment or damping moment may be calculated as the control basis for joint movement, which is not repeated herein.

Figure 8:
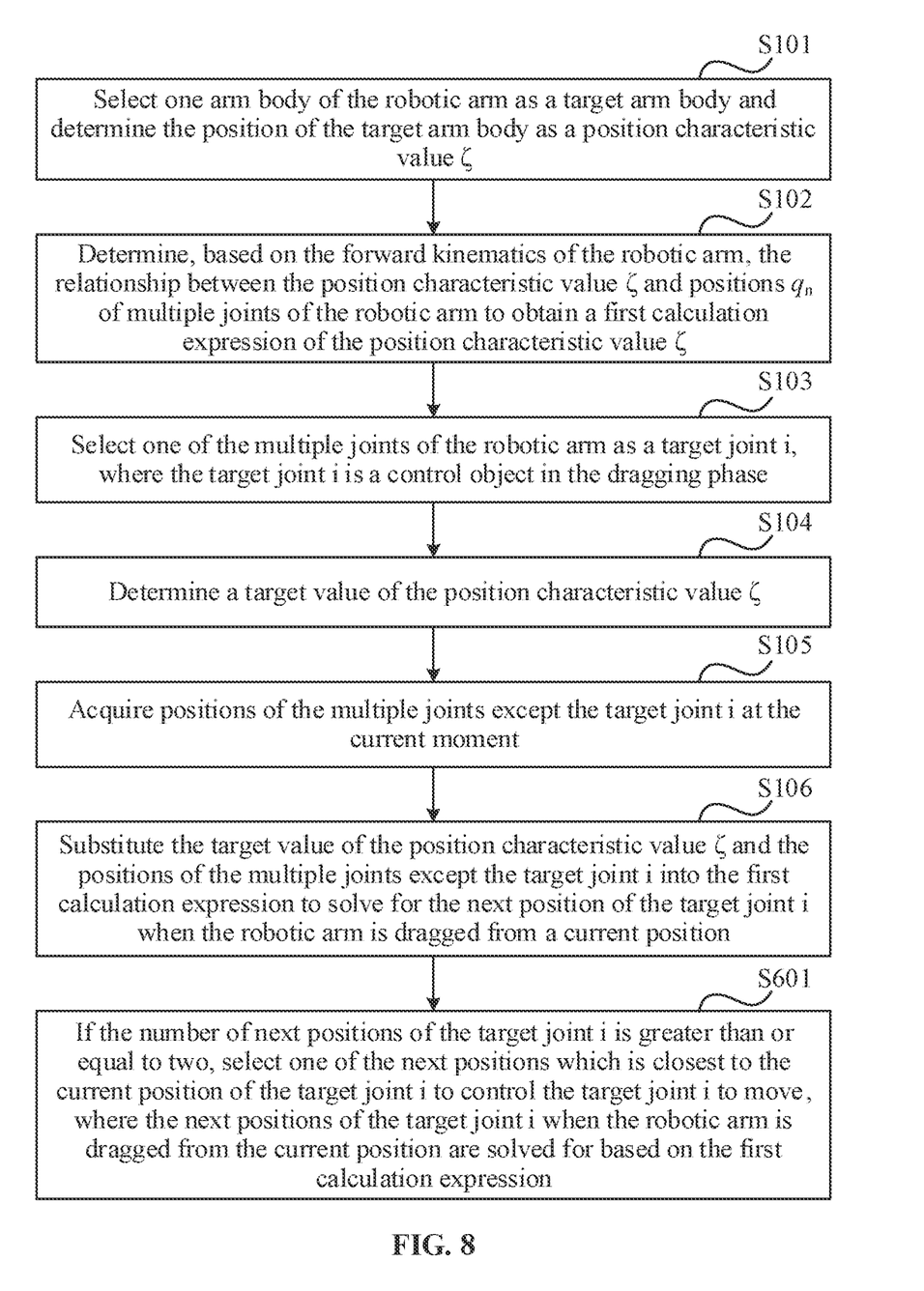
FIG. 8 is a flowchart of yet another robotic arm control method according to an embodiment of the present disclosure.

On the basis of the preceding multiple technical solutions, FIG. 8 is a flowchart of yet another robotic arm control method according to an embodiment of the present disclosure. As shown in FIG. 8, after obtaining the next position of the target joint when the target joint is dragged from the current position in S106, the robotic arm control method also includes the steps below.

In S601, if the number of next positions of the target joint i is greater than or equal to two, one of the next positions which is closest to the current position of the target joint i is selected to control the target joint i to move, where the next positions of the target joint i when the robotic arm is dragged from the current position are solved for based on the first calculation expression.

For example, if the target joint i is a rotating joint, the first calculation expression is a second-order linear equation. In this case, two or more next positions of the target joint i obtained by calculation may exist, that is, the number of solutions of the second-order linear equation is greater than or equal to 2. In the multiple next positions, the next position closest to the current position of the target joint i is selected to move the target joint i. For example, an example is used where the number of the calculated next positions is 2. The calculated next position may be 10° or 170° relative to the ground, and then 10° is selected as the next position of the target joint i to control the movement of the target joint i.

Figure 9:
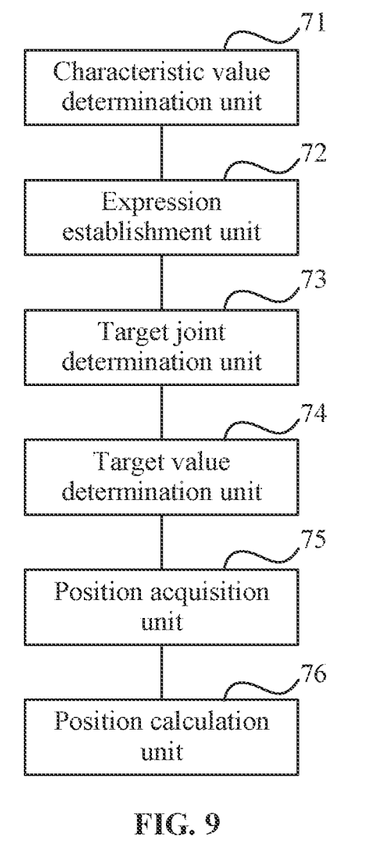
FIG. 9 is a diagram illustrating the structure of a robotic arm control apparatus according to an embodiment of the present disclosure.

FIG. 9 is a diagram illustrating the structure of a robotic arm control apparatus according to an embodiment of the present disclosure. The robotic arm control apparatus is applied to a manual dragging control system of a robotic arm. In the apparatus, the number of joints of the robotic arm is greater than or equal to 4 when the robotic arm moves in a three-dimensional space; the number of joints of the robotic arm is greater than or equal to 3 when the robotic arm moves in a plane. As shown in FIG. 9, the robotic arm control apparatus includes a characteristic value determination unit 71, an expression establishment unit 72, a target joint determination unit 73, a target value determination unit 74, a position acquisition unit 75, and a position calculation unit 76.

The characteristic value determination unit 71 is configured to select one arm body of the robotic arm as a target arm body and determine the position of the target arm body as a position characteristic value.

The expression establishment unit 72 is configured to determine, based on the forward kinematics of the robotic arm, the relationship between the position characteristic value and positions of multiple joints of the robotic arm to obtain a first calculation expression of the position characteristic value.

The target joint determination unit 73 is configured to select one of the multiple joints of the robotic arm as a target joint, and the target joint is a control object in a dragging phase.

The target value determination unit 74 is configured to determine a target value of the position characteristic value.

The position acquisition unit 75 is configured to acquire positions of the multiple joints except the target joint at the current moment.

The position calculation unit 76 is configured to substitute the target value of the position characteristic value and the positions of the multiple joints except the target joint into the first calculation expression to solve for the next position of the target joint when the robotic arm is dragged from a current position.

For example, the characteristic value determination unit 71 is configured to select one arm body of the robotic arm as a target arm body and determine one piece of the following position information of the target arm body as the position characteristic value: the position of the target arm body relative to the ground, the angle of the target arm body relative to the ground, the position of the target arm body relative to another arm body of the robotic arm except the target arm body, or the angle of the target arm body relative to another arm body of the robotic arm except the target arm body.

For example, the expression establishment unit 72 is configured to determine, based on the forward kinematics of the robotic arm, the first calculation expression of the position characteristic value as follows: $\zeta=\zeta(q_1, q_2, \ldots q_n)$. $\zeta$ denotes the position characteristic value; q denotes the position of a joint of the robotic arm; $q_n$ denotes the position of an n-th joint of the robotic arm, $n \in [1, N]$, and N denotes the number of joints of the robotic arm.

For example, the target value determination unit 74 is configured to determine the initial position of the target arm body as the target value of the position characteristic value.

For example, after the position calculation unit 76 obtains the next position of the target joint when the robotic arm is dragged from the current position, the robotic arm control apparatus also includes a movement control unit.

The movement control unit is configured to control the target joint to move based on the calculated next position of the target joint when the robotic arm is dragged from the current position.

For example, after the position calculation unit 76 obtains the next position of the target joint when the robotic arm is dragged from the current position, if the number of next positions of the target joint obtained by the position calculation unit 76 based on the first calculation expression when the robotic arm is dragged from the current position is greater than or equal to two, the movement control unit selects one of the next positions which is closest to the current position of the target joint to control the target joint to move.

The implementation principles and technical effects of the apparatus provided by the embodiments of the present disclosure are the same as those of the preceding method embodiments. For the sake of a brief description, reference may be made to the corresponding content in the preceding method embodiments for parts not mentioned in the apparatus embodiments.

The robotic arm control method provided by the embodiments of the present disclosure has the same technical features as the robotic arm control apparatus provided by the preceding embodiments so that the same situation can be avoided and the same technical effect can be achieved.

Embodiments of the present disclosure also provide a manual dragging control system including the robotic arm control apparatus described in any of the preceding embodiments.

The manual dragging control system provided by the embodiment of the present disclosure includes the robotic arm control apparatus in the preceding embodiments. Therefore, the manual dragging control system provided by the embodiment of the present disclosure also has the beneficial effects described in the preceding embodiments, which is not repeated herein.

Figure 10:
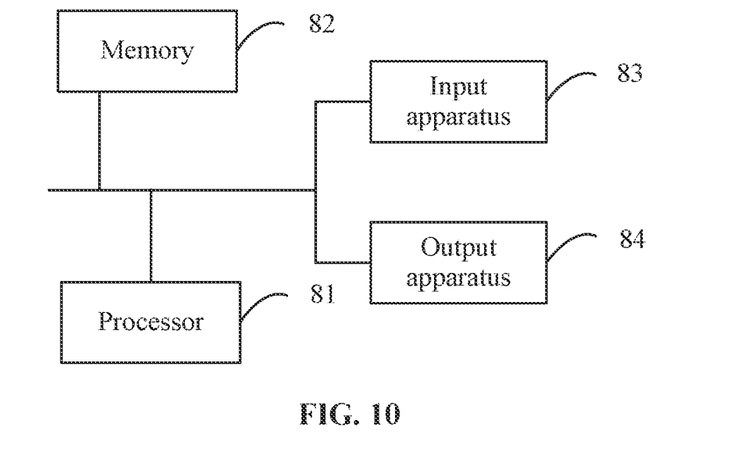
FIG. 10 is a diagram illustrating the structure of a robotic arm according to an embodiment of the present disclosure.

FIG. 10 is a diagram illustrating the structure of a robotic arm according to an embodiment of the present disclosure. As shown in FIG. 10, the robotic arm includes a processor 81, a memory 82, an input apparatus 83, and an output apparatus 84. One or more processors 81 may be provided in the robotic arm. One processor 81 is shown as an example in FIG. 10. The processor 81, the memory 82, the input apparatus 83, and the output apparatus 84 in the robotic arm may be connected via a bus or in other manners. The connection via a bus is shown as an example in FIG. 10.

As a computer-readable storage medium, the memory 82 may be configured to store software programs, computer-executable programs, and modules, such as program instructions/modules (for example, the characteristic value determination unit 71, the expression establishment unit 72, the position acquisition unit 73, and the position calculation unit 74 in the robotic arm control apparatus) corresponding to the robotic arm control method in the embodiments of the present disclosure. The processor 81 executes software programs, instructions, and modules stored in the memory 82 to perform function applications and data processing of the robotic arm, that is, to implement the preceding robotic arm control method. The computer-readable storage medium may be a non-transitory computer-readable storage medium.

The memory 82 may mainly include a program storage area and a data storage area.

The program storage area may store an operating system and an application program required for implementing at least one function while the data storage area may store data created depending on use of terminals. Additionally, the memory 82 may include a high-speed random-access memory and may also include a nonvolatile memory such as at least one disk memory, flash memory, or another non-volatile solid-state memory. In some examples, the memory 82 may include memories that are remotely disposed relative to the processor 81, and these remote memories may be connected to the robotic arm via a network. Examples of the preceding network include, but are not limited to, the Internet, an intranet, a local area network, a mobile communication network, and a combination thereof.

The input apparatus 83 may be configured to receive inputted digital or character information and generate key signal input related to user settings and function control of the robotic arm. The output apparatus 84 may include display devices such as a display screen.

Embodiments of the present disclosure also provide a storage medium containing computer-executable instructions that, when executed by a computer processor, is configured to perform a robotic arm control method.

For example, the robotic arm control method includes a dragging preparation phase and a dragging phase.

The dragging preparation phase includes the steps below.

One arm body of the robotic arm is selected as a target arm body, and the position of the target arm body is determined as a position characteristic value.

Based on the forward kinematics of the robotic arm, the relationship between the position characteristic value and positions of multiple joints of the robotic arm is determined to obtain a first calculation expression of the position characteristic value.

One of the multiple joints of the robotic arm is selected as a target joint, and the target joint is a control object in the dragging phase.

After the dragging preparation phase is completed, the dragging phase is entered, and the dragging phase includes the steps below.

A target value of the position characteristic value is determined.

Positions of the multiple joints except the target joint are acquired at the current moment.

The target value of the position characteristic value and the positions of the multiple joints except the target joint are substituted into the first calculation expression to solve for the next position of the target joint when the robotic arm is dragged from a current position.

Of course, the embodiments of the present disclosure provide a storage medium including computer-executable instructions. The computer-executable instructions may implement not only the operations in the preceding method but also the related operations in the robotic arm control method provided in any embodiment of the present disclosure.

From the preceding description of the embodiments, it is apparent to those skilled in the art that the present disclosure may be implemented by use of software and necessary general-purpose hardware or may be implemented by hardware. Based on this understanding, the technical solutions of the present disclosure substantially, or the part contributing to the related art, may be embodied in the form of a software product. The computer software product may be stored in a computer-readable storage medium such as a floppy disk, a read-only memory (ROM), a random-access memory (RAM), a flash memory, a hard disk, or an optical disk of a computer and includes multiple instructions for causing a computer device (which may be a personal computer, a server, or a network device) to perform the method in multiple embodiments of the present disclosure.

It is to be noted that units and modules involved in the embodiments of the preceding search apparatus are only divided according to functional logic, and the division is not limited to this, as long as the corresponding functions can be achieved. Additionally, the specific names of functional units are only intended for distinguishing and are not to limit the scope of the present disclosure.

In the description of the embodiments of the present disclosure, unless otherwise expressly specified and limited, terms like "mounted", "connected to each other", "connected" are to be construed in a broad sense, for example, as permanently connected, detachably connected, or integratedly connected; mechanically connected or electrically connected; directly connected or indirectly connected via an intermediate medium; or internally connected between two elements. For those of ordinary skill in the art, specific meanings of the preceding terms in the present disclosure can be construed depending on specific contexts.

What is claimed is:

1. A robotic arm control method applied to a manual dragging control system of a robotic arm and comprising a dragging preparation phase and a dragging phase, wherein a number of joints of the robotic arm is greater than or equal to 4 when the robotic arm moves in a three-dimensional space; and a number of joints of the robotic arm is greater than or equal to 3 when the robotic arm moves in a plane;
wherein the dragging preparation phase comprises:
selecting one arm body of the robotic arm as a target arm body and determining a position of the target arm body as a position characteristic value;
determining, based on forward kinematics of the robotic arm, a relationship between the position characteristic value and positions of a plurality of joints of the robotic arm to obtain a first calculation expression of the position characteristic value; and
selecting one of the plurality of joints of the robotic arm as a target joint, wherein the target joint is a control object in the dragging phase;
wherein after the dragging preparation phase is completed, the dragging phase is entered; and
wherein the dragging phase comprises:
determining a target value of the position characteristic value;
acquiring positions of the plurality of joints except the target joint at a current moment; and
substituting the target value of the position characteristic value and the positions of the plurality of joints except the target joint into the first calculation expression to solve for a next position of the target joint when the robotic arm is dragged from a current position.

2. The robotic arm control method of claim 1, wherein the selecting one arm body of the robotic arm as the target arm body and determining the position of the target arm body as the position characteristic value comprise:
selecting the one arm body of the robotic arm as the target arm body; and
determining one piece of position information of the target arm body as the position characteristic value taken from the group consisting of:
a position of the target arm body relative to ground,
an angle of the target arm body relative to ground,
a position of the target arm body relative to another arm body of the robotic arm except the target arm body, and
an angle of the target arm body relative to another arm body of the robotic arm except the target arm body.

3. The robotic arm control method of claim 1, wherein the determining, based on the forward kinematics of the robotic arm, the relationship between the position characteristic value and the positions of the plurality of joints of the robotic arm to obtain the first calculation expression of the position characteristic value comprises:
determining, based on the forward kinematics of the robotic arm, the first calculation expression of the position characteristic value as the following: $\zeta=\zeta(q_1, q_2, \ldots q_n)$, wherein $\zeta$ denotes the position characteristic value, q denotes a position of a joint of the robotic arm, $q_n$ denotes a position of an n-th joint of the robotic arm, $n\in[1, N]$, and N denotes the number of joints of the robotic arm.

4. The robotic arm control method of claim 1, wherein the determining the target value of the position characteristic value comprises:
determining an initial position of the target arm body at the start of dragging as the target value of the position characteristic value.

5. The robotic arm control method of claim 1, wherein after the obtaining the next position of the target joint when the robotic arm is dragged from the current position, the method further comprises:
controlling the target joint to move based on the calculated next position of the target joint when the robotic arm is dragged from the current position.

6. The robotic arm control method of claim 1, wherein after obtaining the next position of the target joint when the robotic arm is dragged from the current position, the method further comprises:
selecting, in response to determining that a number of next positions of the target joint is greater than or equal to two, one of the next positions that is closest to a current position of the target joint to control the target joint to move, wherein the next positions of the target joint when the robotic arm is dragged from the current position are solved for based on the first calculation expression.

7. A manual dragging control system, comprising:
one or more processors; and
a memory configured to store one or more programs;
wherein, when executed by the one or more processors, the one or more programs cause the one or more processors to implement a method as follows:
in a dragging preparation phase:
selecting one arm body of a robotic arm as a target arm body, and determining a position of the target arm body as a position characteristic value;
determining, based on forward kinematics of the robotic arm, a relationship between the position characteristic value and positions of a plurality of joints of the robotic arm to obtain a first calculation expression of the position characteristic value; and
selecting one of the plurality of joints of the robotic arm as a target joint, wherein the target joint is a control object in a dragging phase, and after the dragging preparation phase is completed, the dragging phase is entered; and
in the dragging phase:
determining a target value of the position characteristic value;
acquiring positions of the plurality of joints except the target joint at a current moment; and
substituting the target value of the position characteristic value and the positions of the plurality of joints except the target joint into the first calculation expression to solve for a next position of the target joint when the robotic arm is dragged from a current position;

wherein a number of joints of the robotic arm is greater than or equal to 4 when the robotic arm moves in a three-dimensional space, and wherein a number of joints of the robotic arm is greater than or equal to 3 when the robotic arm moves in a plane.

8. The system of claim 7, wherein when executed by the one or more processors, the one or more programs cause the one or more processors to implement the selecting the one arm body of the robotic arm as the target arm body and determining the position of the target arm body as the position characteristic value by:

selecting the one arm body of the robotic arm as the target arm body; and determining one piece of following position information of the target arm body as the position characteristic value: a position of the target arm body relative to ground, an angle of the target arm body relative to ground, a position of the target arm body relative to another arm body of the robotic arm except the target arm body, or an angle of the target arm body relative to another arm body of the robotic arm except the target arm body.

9. The system of claim 7, wherein when executed by the one or more processors, the one or more programs cause the one or more processors to implement the determining, based on the forward kinematics of the robotic arm, the relationship between the position characteristic value and the positions of the plurality of joints of the robotic arm to obtain the first calculation expression of the position characteristic value by:

determining, based on the forward kinematics of the robotic arm, the first calculation expression of the position characteristic value as the following: $\zeta = \zeta(q_1, q_2, \ldots q_n)$, wherein $\zeta$ denotes the position characteristic value, q denotes a position of a joint of the robotic arm, $q_n$ denotes a position of an n-th joint of the robotic arm, $n \in [1, N]$, and N denotes the number of joints of the robotic arm.

10. The system of claim 7, wherein when executed by the one or more processors, the one or more programs cause the one or more processors to implement the determining the target value of the position characteristic value by:

determining an initial position of the target arm body at the start of dragging as the target value of the position characteristic value.

11. The system of claim 7, wherein when executed by the one or more processors, the one or more programs cause the one or more processors to implement:

controlling, after obtaining the next position of the target joint when the robotic arm is dragged from the current position, the target joint to move based on the calculated next position of the target joint when the robotic arm is dragged from the current position.

12. The system of claim 7 wherein when executed by the one or more processors, the one or more programs cause the one or more processors to implement:

after obtaining the next position of the target joint when the robotic arm is dragged from the current position, in response to determining that a number of next positions of the target joint is greater than or equal to two, selecting one of the next positions that is closest to a current position of the target joint to control the target joint to move, wherein the next positions of the target joint when the robotic arm is dragged from the current position are solved for based on the first calculation expression.

13. A robotic arm, comprising:
a plurality of arm bodies,
a plurality of joints, and
a manual dragging control system comprising:
one or more processors; and
a memory configured to store one or more programs;
wherein when executed by the one or more processors, the one or more programs cause the one or more processors to implement a method as follows:

in a dragging preparation phase:
selecting one arm body of the robotic arm as a target arm body, and determining a position of the target arm body as a position characteristic value;

determining based on forward kinematics of the robotic arm, a relationship between the position characteristic value and positions of the plurality of joints of the robotic arm to obtain a first calculation expression of the position characteristic value; and selecting one of the plurality of joints of the robotic arm as a target joint, wherein the target joint is a control object in a dragging phase, and after the dragging preparation phase is completed, the dragging phase is entered; and in the dragging phase:
determining a target value of the position characteristic value;

acquiring positions of the plurality of joints except the target joint at a current moment; and substituting the target value of the position characteristic value and the positions of the plurality of joints except the target joint into the first calculation expression to solve for a next position of the target joint when the robotic arm is dragged from a current position;

wherein a number of joints of the robotic arm is greater than or equal to 4 when the robotic arm moves in a three-dimensional space; and a number of joints of the robotic arm is greater than or equal to 3 when the robotic arm moves in a plane.

14. The robotic arm of claim 13, wherein when executed by the one or more processors, the one or more programs cause the one or more processors to implement the selecting the one arm body of the robotic arm as the target arm body and determining the position of the target arm body as the position characteristic value by:

selecting the one arm body of the robotic arm as the target arm body; and determining one piece of following position information of the target arm body as the position characteristic value: a position of the target arm body relative to ground, an angle of the target arm body relative to ground, a position of the target arm body relative to another arm body of the robotic arm except the target arm body, or an angle of the target arm body relative to another arm body of the robotic arm except the target arm body.

15. The robotic arm of claim 13, wherein when executed by the one or more processors, the one or more programs cause the one or more processors to implement the determining, based on the forward kinematics of the robotic arm, the relationship between the position characteristic value and the positions of the plurality of joints of the robotic arm to obtain the first calculation expression of the position characteristic value by:

determining, based on the forward kinematics of the robotic arm, the first calculation expression of the position characteristic value as the following: $\zeta = \zeta(q_1,$ $q_2, \ldots q_n$), wherein $\zeta$ denotes the position characteristic value, q denotes a position of a joint of the robotic arm, $q_n$ denotes a position of an n-th joint of the robotic arm, $n \in [1, N]$, and N denotes the number of joints of the robotic arm.

16. The robotic arm of claim 13, wherein when executed by the one or more processors, the one or more programs cause the one or more processors to implement the determining the target value of the position characteristic value by:
determining an initial position of the target arm body at the start of dragging as the target value of the position characteristic value.

17. A non-transitory computer-readable storage medium for storing a computer program that, when executed by a processor, implements the robotic arm control method of claim 1.

18. The storage medium of claim 17, wherein when executed by the processor, the computer program implements the selecting the one arm body of the robotic arm as the target arm body and determining the position of the target arm body as the position characteristic value by:
selecting the one arm body of the robotic arm as the target arm body; and
determining one piece of following position information of the target arm body as the position characteristic value: a position of the target arm body relative to ground, an angle of the target arm body relative to ground, a position of the target arm body relative to another arm body of the robotic arm except the target arm body, or an angle of the target arm body relative to another arm body of the robotic arm except the target arm body.

19. The storage medium of claim 17, wherein when executed by the processor, the computer program implements the determining, based on the forward kinematics of the robotic arm, the relationship between the position characteristic value and the positions of the plurality of joints of the robotic arm to obtain the first calculation expression of the position characteristic value by:
determining, based on the forward kinematics of the robotic arm, the first calculation expression of the position characteristic value as the following: $\zeta = \zeta(q_1, q_2, \ldots q_n)$, wherein $\zeta$ denotes the position characteristic value, q denotes a position of a joint of the robotic arm, $q_n$ denotes a position of an n-th joint of the robotic arm, $n \in [1, N]$, and N denotes the number of joints of the robotic arm.

20. The storage medium of claim 17, wherein when executed by the processor, the computer program implements determining the target value of the position characteristic value by:
determining an initial position of the target arm body at the start of dragging as the target value of the position characteristic value.

\* \* \* \* \*